United States Patent [19]
Suzuki et al.

[11] Patent Number: 5,507,797
[45] Date of Patent: Apr. 16, 1996

[54] SLIDABLE KIT FOR ENDOSCOPIC LIGATION

[75] Inventors: Zenetu Suzuki; Yasunobu Izumi, both of Akita, Japan

[73] Assignee: Sumitomo Bakelite Company Limited, Tokyo, Japan

[21] Appl. No.: 290,128

[22] Filed: Aug. 15, 1994

[30] Foreign Application Priority Data

Aug. 20, 1993 [JP] Japan .................................. 5-206287

[51] Int. Cl.$^6$ .................................................. A61B 17/00
[52] U.S. Cl. ........................................ 606/140; 606/139
[58] Field of Search ........................... 606/140, 141, 606/139, 135, 1, 106, 110, 112, 113, 148, 165; 128/843

[56] References Cited

U.S. PATENT DOCUMENTS

| | | |
|---|---|---|
| 4,375,194 | 4/1983 | Stiegmann . |
| 4,485,817 | 12/1984 | Swiggett ................... 227/180 |
| 5,100,419 | 3/1992 | Ehlers ...................... 606/140 |
| 5,269,789 | 12/1993 | Chin et al. ................ 606/140 |
| 5,320,630 | 6/1994 | Ahmed ..................... 606/139 |

Primary Examiner—Stephen C. Pellegrino
Assistant Examiner—Jeffrey A. Schmidt
Attorney, Agent, or Firm—Browdy and Neimark

[57] ABSTRACT

A slidable kit for endoscopic ligation of gastric and esophageal varices comprises an endoscope-inserting cylinder and a ligating device coaxially and integrally secured to the endoscope-inserting cylinder, where the ligating device is in such a structure that a slide cylinder having an annular rib on the outer periphery at the rearward end is inserted into an outer cylinder having an annular rib on the inner periphery at the forward end; an inner cylinder is inserted into the slide cylinder; the outer cylinder and the inner cylinder are integrated together at the rearward ends and firmly secured to the forward end of the endoscope-inserting cylinder; an elastic O ring is mounted on the outer periphery at the forward end of the inner cylinder; a seal ring is provided at the rearward end of the slide cylinder, thereby keeping an annular space between the outer cylinder, the inner cylinder and the slide cylinder hermetic; the slide cylinder is slidable forwards by a liquid introduced into the annular space through the tube to push and release the elastic O ring, thereby ligating a varix sucked in the inner cylinder, can overcome problems of the conventional kit for endoscopic ligation, such as narrowed endoscopic sight, ligation failure when the endoscope is turned, washing and aspiration failure through a forceps channel.

12 Claims, 3 Drawing Sheets

SLIDABLE KIT FOR ENDOSCOPIC LIGATION

BACKGROUND OF THE INVENTION

1. Field of the Invention

The present invention relates to an instrument for use in endoscopic ligation of varices, thereby blocking mechanical blood circulation to the varices to diminish or vanish or thrombose the ligated varices as one of therapies for gastric and esophageal varices due to hepatic diseases. The present invention provides a very simple instrument for safe endoscopic ligation of varices without fail.

2. Related Prior Art

Gastric and esophageal varices due to hepatic cirrhosis, etc. have been treated mainly according to an endoscopic sclerotherapy by injecting a sclerosing agent having an adverse effect on endothelial cells into varices or into vicinities of varices, thereby making the agent to stay locally at the injected sites and forming thrombi to block blood circulation thereto and decay the varices. However, the intravenous administration of the sclerosing agent having the side effect on the living body has caused complicated blood circulation behaviors such as portal hypertension and also various complications such as pulmonary thrombosis, pulmonary failure, renal failure, etc. Thus, one dose of the sclerosing agent is limited and also the treatment must be carried out in view of recovery of patients, resulting in prolonged treatment.

Figure 4:
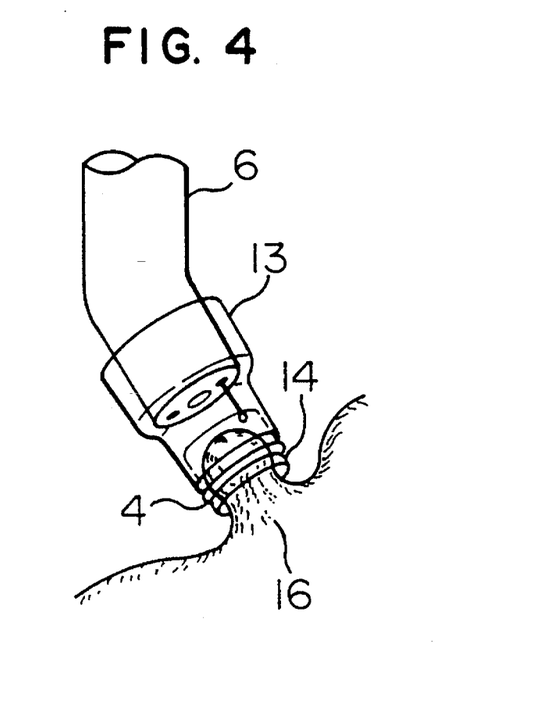
FIG. 4 schematically show a varix sucked into the inner tube of the conventional ligating kit.

Recently, esophageal varix ligation has been used as a therapy for gastric and esophageal varices. As shown in FIG. 4, the esophageal varix ligation is a technique of sucking a varix 16 into a cylindrical device 13 mounted on the forward end of an endoscope 6, releasing an expanded elastic O ring 4 mounted in advance on the outer periphery of the protruded outer periphery of a cylinder 14 inserted into the device 13 from the outer periphery by pulling back the cylinder 14 with a wire inserted through a forceps channel in the endoscope 6, thereby fixing the O-ring around the basis of sucked polyp-like varix and mechanically ligating and decaying the varix by the contracting force of the expanded O-ring 4. The forward end of the cylinder 14 is protruded from the forward end of the device 13.

Ligating kit now in use for this purpose will be explained in detail-below, referring to FIG. 3.

Figure 3:
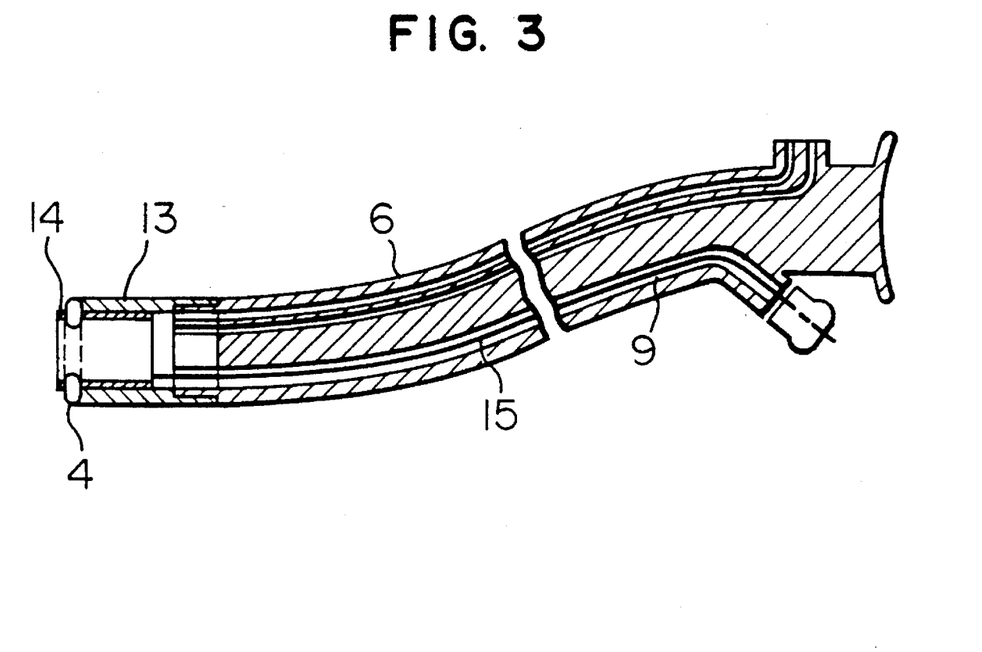
FIG. 3 is a crosssectional view showing the conventional ligating kit mounted on an endoscope.

FIG. 3 schematically shows the structure of a ligating kit now in practical use.

A cylinder 14 provided with an expanded elastic O ring 4 on the outer periphery at the forward end is inserted into a cylindrical device 13 fixed to the forward end of an endoscope 6, while the forward end of the cylinder 14 provided with the expanded O ring 4 on the outer periphery is protruded from the forward end of the cylindrical device 13. A wire 15 is connected to the cylinder 14 through the forceps channel 9 in the endoscope 6, and the cylinder 14 can be pulled back by pulling the wire 15, whereby the expanded O ring 4 is released from the forward end of the cylinder 14.

Increased use of esophageal varix ligation will be expected because no sclerosing agent is used at all or the dose of sclerosing agent can be reduced, even if the sclerotherapy is applied together at the same time, with the result that complications can be reduced and a burden on patients can be lessened or number or duration of treatment can be reduced. However, in the case of sucking a varix 16 into the device 13, vertical access of the device 13 to a varix 16 to surround it is preferable, because inclined access often give rise to a gap in the surrounding of varix, resulting in insufficient suction and failure to ligate the varix.

Furthermore, the kit for use in the esophageal varix ligation has various problems. For example, the endoscopic sight is narrowed because the device 13 is fixed to the forward end of the endoscope 6. In the case of ligation of gastric varices on the convexity of stomach, the endoscope must be turned for the ligation, and when there is bleeding from the varices, the blood often accumulates in the device 13, losing the endoscopic sight. Wire 15 for releasing the expanded O ring 4 is extended to the forward end of the endoscope through the forceps channel 9 in the endoscope 6, and thus washing of stomach and esophagus or aspiration of washing solution therefrom through the forceps channel cannot be carried. It would be possible to use an endoscope with two forceps channels, but most of hospitals are equipped with endoscopes only with one channel and not with two channels and thus cannot promptly meet such requirements.

Furthermore, when the endoscope is turned, the wire 15 fails to smoothly slide through the forceps channel 9 due to the friction, and sometimes the expanded O ring fails to be released even by pulling back the wire 15. Particularly for ligating varices on the convexity of stomach it is inevitable to turn the endoscope, but in the actual practice the device 13 is given inclined access to a varix to ligate it without turning or with least turning of the endoscope 6.

SUMMARY OF THE INVENTION

An object of the present invention is to provide a ligating kit that has solve the problems encountered in the conventional ligating kit for use in the endoscopic gastric and esophageal varix ligation, such as narrowed endoscopic sight, failure to conduct washing or aspiration through the forceps channel and failure to ligate the varix when the endoscope is turned.

Another object of the present invention is to provide a ligating kit that permits an operation to conduct ligation safely without fail.

According to a first aspect of the present invention, there is provided a slidable kit for endoscopic ligation of gastric and esophageal varices, which comprises:

a) an outer cylinder having a rib on the inner periphery at the forward end;

b) a slide cylinder having a rib on the outer periphery at the rearward end, inserted into the outer cylinder;

c) an inner cylinder inserted into the slide cylinder, a rib being provided on at least one of the inner periphery at the rearward end of the outer cylinder and the outer periphery at the rearward end of the inner cylinder, through which the outer cylinder and the inner cylinder are integrated, d) a cylinder for fixing to an endoscope, the forward end of the cylinder being firmly secured to the rearward end of the integrated outer cylinder and the inner cylinder;

e) an elastic O ring expanded and mounted on the outer periphery at the forward end of the inner cylinder;

f) a seal ring provided at the rearward end of the inner cylinder, whereby an annular hermetic space is formed between the rearward ends of the outer cylinder, the inner cylinder and the slide cylinder;

g) a throughhole provided through the rearward end of the annular hermetic space; and h) a tube connected to the throughhole and serving as a fluid passage, a fluid being introduced under pressure into the annular hermetic space through the tube, thereby sliding the slide cylinder forwards releasing the expanded O ring from the forward end of the inner cylinder by pushing with the slide cylinder and ligating a varix sucked in the inner cylinder with the released O ring.

In the kit according to the first aspect of the present invention the inner cylinder and the slide cylinder can be extended in the axial direction; a second outer cylinder having ribs at the forward end and the rearward end can be firmly secured on the outer periphery of the extended part of the slide cylinder while the forward end part of the extended slide cylinder is protruded from the forward end of the second outer cylinder; the elastic O ring can be expanded and mounted on the outer periphery of the protruded forward end part of the slide cylinder; a second slide cylinder having a rib at the rearward end can be inserted between the second outer cylinder and the extended inner cylinder; a second seal ring can be provided at the rearward end of the second slide cylinder, whereby a second annular hermetic space is formed between the rearward ends of the second outer cylinder, the extended slide cylinder and the second slide cylinder; a second throughhole can be provided at the rearward end of the second annular hermetic space; and a second tube connected to the second throughhole and serving a second fluid passage; the fluid can be also introduced into the second annular hermetic space through the second tube from the outside source, thereby sliding the second slide cylinder forwards, releasing the expanded elastic O ring from the protruded forward end part of the slide cylinder and ligating a varix sucked in the inner cylinder with the released elastic O ring.

According to a second aspect of the present invention there is provided a single slidable kit for endoscopic ligation of gastric and esophageal varices, which comprises an endoscope-inserting cylinder and a ligating device coaxially and integrally secured to the endoscope-inserting cylinder;

the legating device comprising:

(a) an outer cylinder having an annular forward end rib on the inner periphery at the forward end;

(b) a slide cylinder having an annular rearward end rib on the outer periphery at the rearward end, inserted into the outer cylinder to a deepest position and supported by the annular forward end rib of the outer cylinder, the annular rearward end rib being reciprocally slidable in the axial direction along the inner periphery of the outer cylinder;

(c) an inner cylinder inserted into the outer cylinder through the slide cylinder therebetween, the forward end of the inner cylinder being protruded from the annular forward end of the outer cylinder, an annular rearward end rib being provided on at least one of the inner periphery at the rearward end of the outer cylinder and the outer periphery at the rearward end of the inner cylinder, the outer cylinder and the inner cylinder being integrally and firmly secured to each other through the annular rearward end rib;

(d) a seal ring provided at the rearward side of the annular rearward end rib of the slide cylinder and in contact with the inner periphery of the outer cylinder and the outer periphery of the inner cylinder, whereby an annular hermetic space is formed between the inner side of the annular rearward end rib of the integrally secured outer cylinder and inner cylinder, the inner periphery of the outer cylinder and the outer periphery of the inner cylinder; and (e) an elastic O ring expanded and mounted on the protruded forward end part of the inner cylinder from the forward end of the outer cylinder;

the endoscope-inserting cylinder having a throughhole for hermetically inserting an endoscope up to the forward end, coaxially and firmly secured to the rearward end of the ligating device, the throughhole being penetrated in the axial direction from the rearward end to the forward end;

a tube channel being provided through the wall of the endoscope-inserting cylinder and the rearward end of the ligating device into the annular hermetic space, whereby the annular hermetic space is communicated with an outer tube, through which a fluid is introduced under pressure to the annular hermetic space from an outside source, thereby sliding the slide cylinder forwards and releasing the expanded elastic O ring from the protruded forward end part of the inner cylinder by pushing the O-ring with the slide cylinder and ligating a varix sucked in the inner cylinder with the released elastic O ring.

In the single slidable kit according to the second aspect of the present invention, the annular rearward end rib can be provided each on the outer periphery of the inner cylinder and the inner periphery of the outer cylinder, the annular rearward end rib provided on the inner periphery of the outer cylinder can be longer forwards than the annular rearward end rib provided on the outer periphery of the inner cylinder, thereby defining the deepest position of the annular rearward end rib of the inserted slide cylinder; the annular rearward end rib can be provided on the outer periphery of the outer cylinder, the rearward side of which can be flat and the forward side of which can be in an L-shaped structure where the bottom end can be protruded forwards beyond the top end, thereby defining the deepest position of the annular rearward end rib of the inserted slide cylinder; a spring can be inserted in the axial direction in a space formed between the annular forward end rib of the outer cylinder and the annular rearward end rib of the slide cylinder; and the rearward end of the outer tube can be connected to a syringe through a connector.

According to a third aspect of the present invention, there is provided a double slidable kit for endoscopic ligation of gastric and esophageal varices, which comprises an endoscope-inserting cylinder and a ligating device coaxially and integrally secured to the endoscope-inserting cylinder;

the legating device comprising:

(a) a first outer cylinder having an annular forward end rib on the inner periphery at the forward end;

(b) a first slide cylinder having an annular rearward end rib on the outer periphery at the rearward end, inserted into the first outer cylinder to a deepest position and supported by the annular forward end rib of the first outer cylinder, the annular rearward end rib being reciprocally slidable in the axial direction along the inner periphery of the first outer cylinder, the forward end of the first slide cylinder being protruded from the forward end of the first outer cylinder;

(c) an inner cylinder inserted into the first outer cylinder through the first slide cylinder therebetween, the forward end of the inner cylinder being protruded from the annular forward end of the first outer cylinder to the substantially same position as the forward end of the first slide cylinder at the deepest position, an annular rearward end rib being provided on at least one of the inner periphery at the rearward end of the first outer cylinder and the outer periphery at the rearward end of the inner cylinder, the first outer cylinder and the inner cylinder being integrally and firmly secured to each other through the annular rearward end rib;

(d) a first seal ring provided at the rearward side of the annular rearward end rib of the first slide cylinder and in contact with the inner periphery of the first outer cylinder and the outer periphery of the inner cylinder, whereby a first annular hermetic space is formed between the inner side of the annular rearward end rib of the integrally secured first outer cylinder and inner cylinder, the inner periphery of the first outer cylinder and the outer periphery of the inner cylinder;

(e) a second outer cylinder having an annular forward end rib on the inner periphery at the forward end being provided on the outer periphery of the protruded part of the first slide cylinder, the protruded part of the first slide cylinder being further protruded from the forward end of the second outer cylinder;

(f) a second slide cylinder having an annular rearward end rib on the outer periphery at the rearward end, inserted into the second outer cylinder to a deepest position and supported by the annular forward end rib of the second outer cylinder, the annular rearward end rib being reciprocally slidable in the axial direction along the inner periphery of the second outer cylinder, an annular rearward end rib being provided on the inner periphery at the rearward end of the second outer cylinder, the second outer cylinder being integrally and firmly secured to the first slide cylinder through the annular reward end rib;

(g) a second seal ring being provided at the rearward side of the annular rearward end rib of the second slide cylinder and in contact with the inner periphery of the second outer cylinder and the outer periphery of the first slide cylinder, whereby a second annular hermetic space is formed between the inner side of the annular rearward end rib of the second outer cylinder, the inner periphery of the second outer cylinder and the outer periphery of the first slide cylinder; and (h) an elastic O ring expanded and mounted on the protruded forward end part of the first slide cylinder from the forward end of the second outer cylinder;

the endoscope-inserting cylinder having a throughhole in the axial direction and being coaxially and firmly secured to the rearward end of the ligating device, the throughhole having the same diameter as that of the inner cylinder, through which an endoscope is hermetically insertable from the rearward end of the endoscope-inserting cylinder to the forward end of the inner cylinder;

a first tube channel being provided through the wall of the endoscope-inserting cylinder and the rearward end of the ligating device into the first annular hermetic space, whereby the first annular hermetic space is communicated with a first outer tube, through which a fluid is introduced under pressure to the first annular hermetic space from an outside source, thereby sliding the first slide cylinder forwards, protruding the first slide cylinder from the forward end of the inner cylinder and forming a varix suction hole inside the protruded first slide cylinder;

a second tube channel being provided through the annular rearward end rib of the second outer cylinder into the second annular hermetic space, whereby the second annular hermetic space is communicated with a second outer tube, through which a fluid is introduced under pressure to the second annular hermetic space from an outside source, thereby sliding the second slide cylinder forwards and releasing the expanded elastic O ring from the protruded forward end part of the first slide cylinder by pushing the elastic O ring with the second slide cylinder and ligating a varix sucked in the protruded first slide cylinder with the released elastic O ring.

In the double slidable kit according to the third aspect of the present invention, the annular rearward end rib can be provided each on the outer periphery of the inner cylinder and the inner periphery of the first outer cylinder, the annular rearward end rib provided on the inner periphery of the first outer cylinder can be longer forwards than the annular rearward end rib provided on the outer periphery of the inner cylinder, thereby defining the deepest position of the annular rearward end rib of the inserted first slide cylinder; the annular rearward end rib can be provided on the outer periphery each of the first and second outer cylinders, the rearward side of which can be flat and the forward side of which can be in an L-shaped structure where the bottom end can be protruded forwards beyond the top end, defining the deepest position of the annular rearward end rib of the inserted first and second slide cylinders; a spring can be inserted each in the axial direction in spaces formed between the annular forward end ribs of the first and second outer cylinder and the annular rearward end ribs of the first and second slide cylinder, respectively; and the rearward ends of the first and second outer tubes can be connected to syringes through connectors, respectively.

BRIEF DESCRIPTION OF THE DRAWINGS

FIGS. 1A and 1B schematically show a single slidable kit for endoscopic ligation according to one embodiment of the present invention, where

FIGS. 2A and 2B schematically show a double slidable kit for endoscopic ligation according to another embodiment of the present invention, where

PREFERRED EMBODIMENTS OF THE INVENTION

The present invention will be described in detail below, referring to the drawings.

Figure 1A:
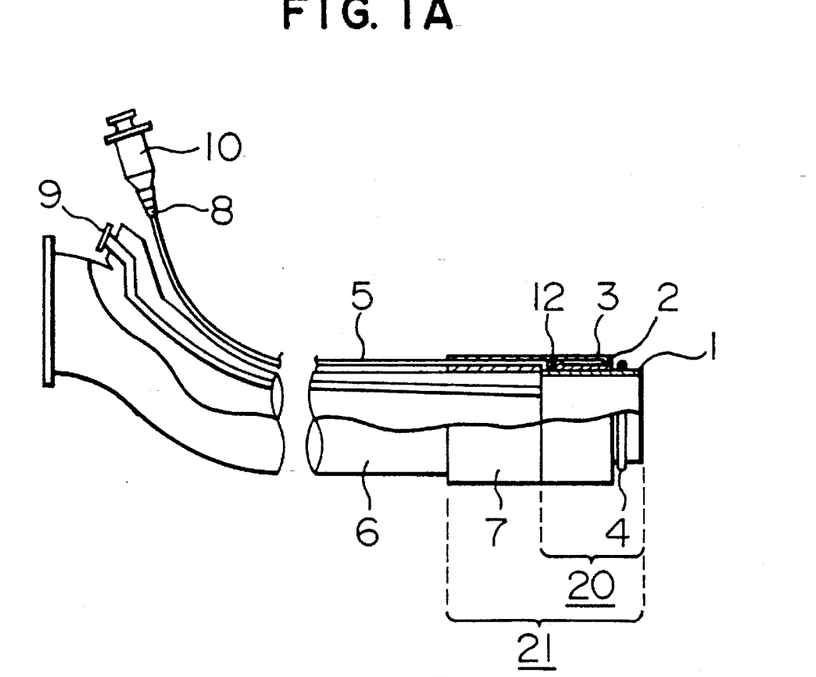
FIG. 1A is a partly cutaway view showing the kit with an endoscope inserted therein and FIG. 1B is an enlarged, partly cutaway view thereof.
Figure 1B:
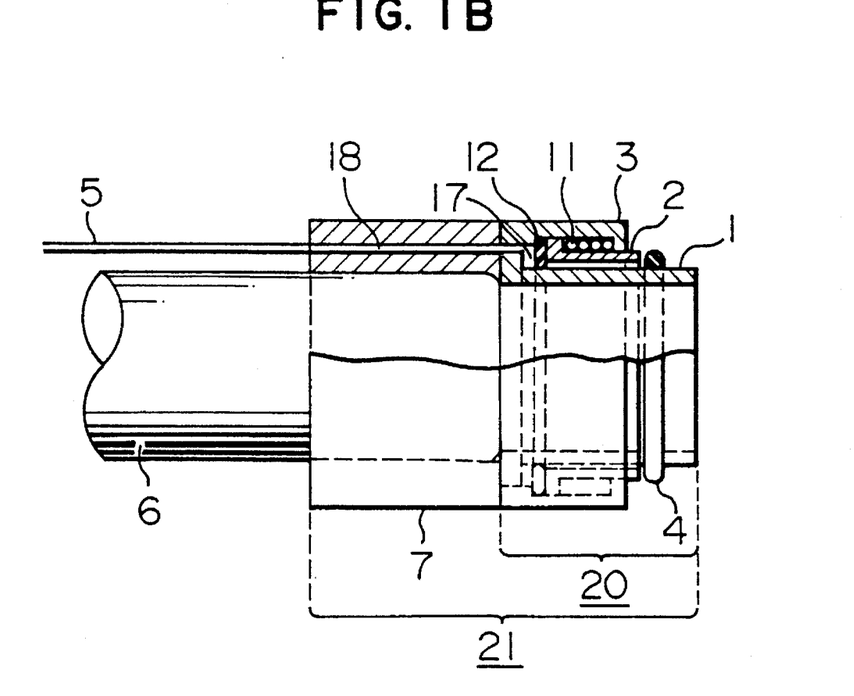

As shown in FIGS. 1A and 1B, a slidable kit 21 for endoscopically ligating gastric and esophageal varices comprises an endoscope-inserting cylinder 7 and a ligating device 20 coaxially and firmly secured to the cylinder 7 as essential members.

Particularly, when the slidable kit 21 is in a single slidable structure the ligating device 20 is in the following structure as shown in FIGS. 1A and 1B:

A slide cylinder 2 having an annular rearward end rib on the outer periphery at the rearward end is inserted into an outer cylinder 3 having an annular forward end rib on the inner periphery at the forward end to a deepest position in the outer cylinder 3, where the annular rearward end is reciprocally slidable in the axial direction along the inner periphery of the outer cylinder 3, and the forward end of the slide cylinder 2 is supported by the annular forward end rib of the outer cylinder 3.

Furthermore, an inner cylinder 1 is inserted into the outer cylinder 3 through the slide cylinder 2, and the forward end of the inner cylinder 1 is protruded from the forward end of the outer cylinder 3.

An annular rearward end rib is provided on at least one of the inner periphery at the rearward end of the outer cylinder 3 and the outer periphery at the rearward end of the inner cylinder 1, and the outer cylinder 3 and the inner cylinder 1 are integrally and firmly secured to each other with the annular rearward rib, thereby forming the ligating device 20.

In FIG. 1B, the annular rearward end rib is provided each on the inner periphery of the outer cylinder 3 and on the outer periphery of the inner cylinder 1, where the annular rearward rib of the outer cylinder 3 is longer forwards than that of the inner cylinder 1 and defines the deepest position of the annular rearward end rib of the slide cylinder 2.

The annular rearward end rib of the outer cylinder 3 can be in an L-shaped structure, where the bottom end is longer forwards than the top end, that is, is protruded forwards beyond the top end to define the deepest position of the annular rearward end rib of the slide cylinder 2.

The rearward end of the ligating device 20 formed by integrally and firmly securing the outer cylinder 3 and the inner cylinder 1 to each other at the rearward ends, while the slide cylinder 2 is inserted between the outer cylinder 3 and the inner cylinder 1, is further coaxially secured to the forward end of the endoscope-inserting cylinder 7, whereby the throughhole of the inserting cylinder 7 and the throughhole of the inner cylinder 1 are coaxially fitted to each other to form a common throughhole penetrated throughout the kid 21.

The outer cylinder 3 and the inner cylinder 1 are firmly secured to each other and kept stationary, whereas the slide cylinder 2 is reciprocally slidable in the axial direction, and its slide stroke is defined by the distance between the annular forward end rib of the outer cylinder 3 and the annular rearward rib on at least one of the inner periphery of the outer cylinder 3 and the outer periphery of the inner cylinder 1 at the rearward end.

An elastic O ring is expanded and mounted on the outer periphery of the protruded forward end part of the inner cylinder 1 from the forward end of the outer cylinder 3. On the other hand, a seal ring 12 is provided at the rearward end of the slide cylinder 2 and in contact with the inner periphery of the outer cylinder 3 and the outer periphery of the inner cylinder 1, whereby an annular hermetic space 17 is formed between the inner side of the rearward end of the integrally secured outer cylinder 3 and inner cylinder 1, the inner periphery of the outer cylinder 3 and the outer periphery of the inner cylinder 1.

A tube channel 18 is provided through the wall of the endoscope-inserting cylinder 7 and the rearward end of the ligating device 20, integrally and firmly secured to each other, as described above, into the annular hermetic space 17, whereby the annular hermetic space 17 is communicated with an outer tube 5, through which a fluid is introduced under pressure to the annular hermetic space 17 from an outside sourse, thereby sliding the slide cylinder 2 forwards and releasing the elastic O ring 4 from the protruded forward end part of the inner cylinder 1 by pushing the expanded elastic O ring 4 with the slide cylinder 2 and ligating a varix sucked in the inner cylinder 1 with the released O ring 4.

The annular hermetic space 17 and the outer tube 5 communicating with the annular hermetic space 17 through the tube channel 18 are kept hermetically so as not to leak out the fluid introduced under pressure.

The present slidable ligating kit 21 is used by inserting the forward end of an endoscope 6 into the throughhole of the endoscope-inserting cylinder 7 and firmly securing it thereto. Thus, the endoscope-inserting cylinder 7 must be less disengageable from the inserted endoscope 6 and air must be hard to leak through between the cylinder 7 and the endoscope 6 when a varix 16 is sucked into the inner cylinder under reduced pressure. However, too tight engagement of the cylinder 7 with the endoscope 6 is more liable to give an adverse effect on the endoscope 6. Thus, materials for the cylinder 7 preferably have appropriate softness and sealability. Preferable materials for the cylinder 7 are soft plastics, rubber, etc., but are not particular limited thereto.

When the forward end of the endoscope is inserted to and firmly secured to the present slidable ligating kit 21, the outer tube 5 is extended along the outer periphery of the endoscope 6 a little beyond the rearward end of the endoscope up to the hands of an operator. When the fluid is to be introduced under pressure to the annular hermetic space 17, the outer tube 5 is connected to a fluid pumping device such as a syringe 10 through a connector 8 provided at the rearward end of the outer tube 5. To prevent the introduced fluid from leakage, a blocking mechanism such as a check valve may be provided at the connector 8. Terminal end of the connector 8 is preferably luer-tapered, but the shape of the terminal end is not particularly limited, because the connector type may be changed, depending on a fluid pumping procedure.

The outer tube 5 must have an appropriate pressure resistance, a good fittability to the connector 8, the outer cylinder 3 and the inner cylinder 1 and an appropriate corresponding flexibility to bending of the endoscope 6, and thus materials for the outer tube 5 are soft plastics, rubber, etc., but are not particularly limited thereto.

It is also preferable that the outer tube 5 has as small an outer diameter as possible and gives neither voluminous nor mismatched appearance when the outer tube 5 is extended along the outer periphery of the endoscope 6. However, it is necessary that the fluid must be passed therethrough to the forward end thereof without fail. Thus, the outer tube 5 must have an inner diameter of 0.5–1.5 mm and can have not only a circular cross-section, but also an elliptical cross-section. Furthermore, the outer tube 5 must have at least a sufficient length to extend from the forward end of the endoscope 6 a little beyond the rearward end of the forceps channel 9, but is not particularly limited, so far as it has an appropriate length to allow easy handling by an operator.

Materials for the outer cylinder 3, the slide cylinder 2 and the inner cylinder 1, which constitute the ligating device 20 of the present slidable kit 21, preferably have a good slidability to give smooth sliding to the slide cylinder 2, a good processability to give exact dimension and appropriate clearances to the respective cylinders when brought into mutual contact, and less thermal deformation at pasteurization or at climatic temperature or body temperature. Thus, preferable materials are metals such as stainless steel, rigid plastics, etc., but are not particularly limited thereto.

The forward end of the slidable kit 21 for sucking a varix 16 into the inner cylinder 1 preferably has an inner diameter of 5–12 mm and 5–15 mm long, but is not particularly limited thereto. The larger the inner diameter, the larger the outer diameter, resulting in difficult passage of the slidable kit 21 secured to the endoscope 6 through the oral cavity and pharynx region of a patient. Since the ordinary endoscope 6 has an outer diameter of 7–13 mm, it is preferable that the maximum outer diameter of the slidable kit 21 secured to the endoscope 6 is limited to the outer diameter of the endoscope plus about 1—about 3 mm. The smaller the outer diameter of the slidable kit 21, the smaller the wall thickness of the cylinders 1, 2 and 3 that constitute the kit 21. Thus, there will be problems of cylinder strength such as easy breaking, etc. That is, it is important to determine the dimensions of the kit 21 in view of selected materials.

The inner cylinder 1 must be longer than the outer cylinder 3, because the O ring 4 is mounted on the outer periphery of the protruded forward end part of the inner cylinder 1 from the forward end of the outer cylinder 3, and the slide cylinder 2 must have a sufficient length to push the O ring 4 to release it from the protruded forward end of the inner cylinder 1 by sliding the slide cylinder 2 forwards.

The present single slidable kit 21 for endoscopic ligation is used as follows:

At first, the outer periphery of a fiber of endoscope 6 is coated with xylocaine jerry (trademark of lidocaine jelly), etc. and the endoscope 6 is inserted into a guide tube for passing the endoscope through the pharynx region of a patient and set thereto. Then, only the endoscope is inserted into the pharynx region of a patient to allow its forward end to reach the region. Then, the guide tube is slided down along the inserted endoscope 6 and inserted into the pharynx region, and the mouthpiece provided at the rearward end of the guide tube is held between the teeth of the patient to allow the guide tube to stay there.

Then, the endoscope 6 is withdrawn from the guide tube and the forward end of the endoscope 6 is inserted into the throughhole of the single slidable kit 21. The outer tube 5 is extended along the outer periphery of the endoscope 6 and, if necessary, fixed thereto, with a tape or the like. Then, the elastic O ring 4 is expanded and mounted on the protruded forward end part of the inner cylinder 1, and then the endoscope 6 secured to the single slidable kit 21 is again inserted to a site of varix 16 to be ligated through the guide tube. The forward end of the kit 21 is given as vertical access as possible to the ligating site to allow the inner tube 1 to surround the varix. The varix 16 is then sucked into the inner tube 1 at the forward end of the kit 21 by an aspirator attached to the endoscope 6. When the polyp-shaped varix 16 sucked into the sight of the endoscope 6 is witnessed to turn red through the endoscope 6, a fluid is introduced under pressure into the annular hermetic space 17 through the outer tube 5 from a syringe 10 or the like, for example, by pushing down the syringe piston, thereby pushing the slide cylinder 2 to slide it forwards, push and release the expanded elastic O ring 4 from the protruded forward end of the inner cylinder (1), thereby legating the sucked varix 16 with the released elastic O ring 4.

The endoscope 6 is withdrawn from the guide tube after each ligation and a new elastic O ring 4 must be mounted onto the protruded forward end part of the inner cylinder 1. The endoscope 6 can easily be inserted or withdrawn through the pharynx region to or from a ligating site because of the use of the guide tube. When a liquid is used as the fluid, it is necessary to remove air from the annular hermetic space 17, and the outer tube 5 in advance. That is, air is replaced with the liquid before inserting the endoscope 6 into the throughhole of the present slidable kit 21.

For reuse of the present slidable kit 21 after the ligation by releasing the elastic O ring 4, the syringe piston is pulled back to withdraw the liquid filled in the annular hermetic space 17, thereby pulling back the slide cylinder 2. Usually, the slide cylinder 2 can be retreated spontaneously by discharging or withdrawing the fluid from the outer tube 5, but in the case the slide cylinder 2 is hard to retreat, a spring 11 is provided in the axial direction in the space between the annular forward end rib of the outer cylinder 3 and the annular rearward end rib of the slide cylinder 2, as shown in FIG. 1B. When the slide cylinder 2 fails to slide smoothly, silicone oil, etc. can be applied to the contact parts between the slide cylinder 2 and the outer cylinder 3.

In the embodiment shown in FIGS. 1A and 1B, the forward end of the endoscope 6 is positioned at the rearward end of the ligating device 20, when inserted into the throughhole 21, and thus the sight of the endoscope 6 is somewhat narrowed. To solve the narrowed sight, the slide cylinder of the ligating device 20 is made into a double slidable structure, as shown in FIGS. 2A and 2B.

Figure 2A:
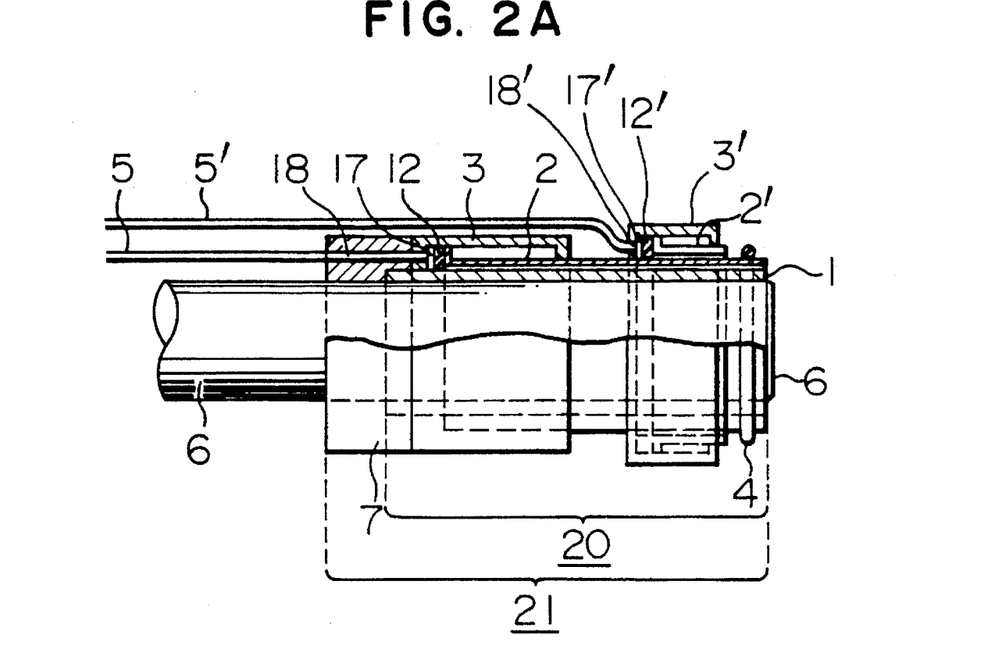
FIG. 2A is a partly cutaway view showing the double slidable kit with an endoscope inserted therein in an initial stationary state and FIG. 2B is a partly cutaway view of the double slidable kit in a state after first slide action.
Figure 2B:
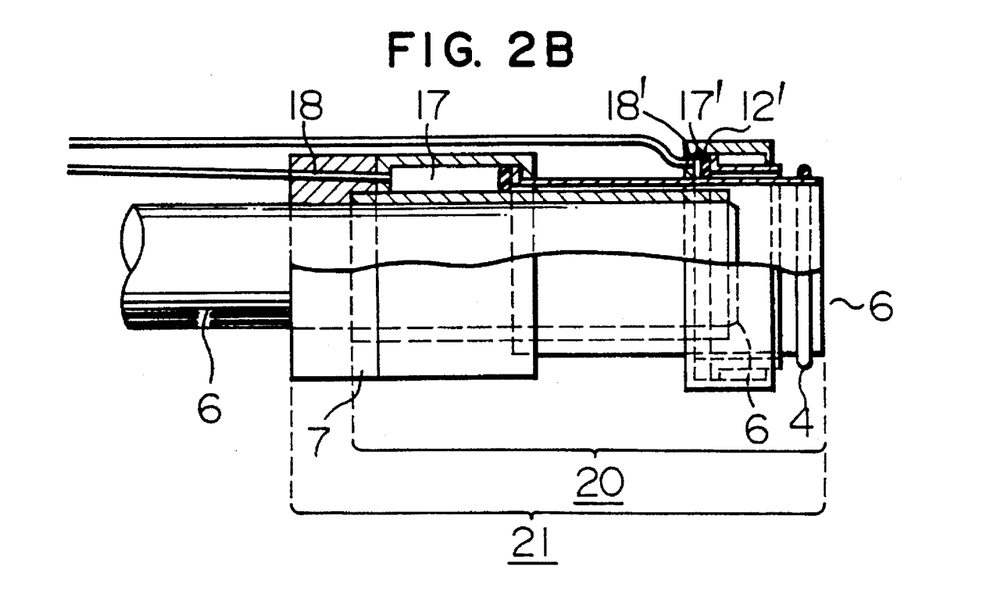

In the double slidable structure as shown in FIGS. 2A and 2B, the inner cylinder 1 and the slide cylinder 2 are extended in the axial direction, and a second outer cylinder 3' and a second slide cylinder 2' are provided in combination on the outer periphery of the extended slide cylinder 2. An annular hermetic space 17' between the inner periphery of the second cylinder 3', the rearward end of the second slide cylinder, and the inner periphery of the extended slide cylinder 2 is made hermetic by a seal ring 12' provided at the rearward end of the second slide cylinder 2', and connected to a second outer tube 5' to introduce a fluid thereto under pressure, independly from the annular hermetic space 5. The forward end of the endoscope 6 is inserted to the forward end of the extended inner cylinder 1 of the slidable kit 21, and is kept hermetic at the forward end of the inner cylinder 1 of the slidable kit 21.

That is, a double slidable kit 21 for endoscopic ligation of gastric and esophageal varices, as shown in FIGS. 2A and 2B, comprises an endoscope-inserting cylinder 7 and a ligating device 20 coaxially and integrally secured to the endoscope-inserting cylinder 7.

The ligating device 20 is in the following structure.

A first slide cylinder 2 having an annular rearward end rib on the outer periphery at the rearward end is inserted into a first outer cylinder 3 having an annular forward end rib on the inner periphery at the forward end to a deepest position in the first outer cylinder 3. The annular rearward end rib of the first slide cylinder 2 is reciprocally slidable along the inner periphery of the first outer cylinder 3 in the axial direction, and the first slide cylinder 2 is supported at the annular forward end rib of the outer cylinder 3. The forward end of the first slide cylinder 2 is protruded from the forward end of the first outer cylinder 3.

An inner cylinder 1 is inserted into the first outer cylinder 3 through the first slide cylinder 2, and the forward end of the inner cylinder is protruded from the forward end of the first outer cylinder 3 to substantially the same position as that of the first slide cylinder 2 inserted to the deepest position in the first outer cylinder 3.

An annular rearward end rib is provided on at least one of the inner periphery at the rearward end of the first outer cylinder 3 and the outer periphery of the inner cylinder 1. The first outer cylinder 3 and the inner cylinder 1 are firmly secured to each other with the annular rearward end rib to form the basic body of a ligating device 20. In FIGS. 2A and 2B, the annular rearward end rib is provided only on the inner periphery at the rearward end of the first outer cylinder 3, but as shown in FIG. 1B, the annular rearward end rib can be provided on both of the inner periphery of the first outer cylinder 3 and the outer periphery at the rearward end of the inner cylinder 1, and the annular rearward end rib on the inner periphery of the first outer cylinder 3 can be extended forwards from that on the outer periphery of the inner cylinder 1 to define the deepest position of the annular rearward rib of the first slide cylinder 2.

The basic body of the ligating device 20 formed by integrally securing the first outer cylinder 3 and the inner cylinder 1 to each other at the rearward ends, with the first slide cylinder 2 inserted there-between, as described above, is coaxially and firmly secured to the forward end of the endoscope-inserting cylinder 7 to coaxially match the throughhole of the cylinder 7 with that of the inner cylinder 7, thereby forming a common throughhole. In FIGS. 2a and 2B, the rearward end of the inner cylinder 1 is rearwardly extended from the rearward end of the first outer cylinder 3, and the rearwardly extended part of the inner cylinder 1 is inserted into an annular recess having a size corresponding to the outer diameter of the inner cylinder 1, provided at the forward end of the cylinder 7, to easily secure the basic body of the ligating device 20 to the cylinder 7 and easily obtain the common throughhole.

The first outer cylinder 3 and the inner cylinder 1 are firmly secured to each other and made to stay stationary, whereas the first slide cylinder 2 is reciprocally slidable along the inner periphery of the first outer cylinder 3 in the axial direction, and its slide stroke is determined by the distance between the annular forward end rib of the first outer cylinder 3 and the annular rearward rib on at least one of the inner periphery of the first outer cylinder 3 and the outer periphery of the inner cylinder 1 at the rearward ends.

A first seal ring 12 is provided at the rearward side of the annular rearward end rib of the first slide cylinder 2 and in contact with the inner periphery of the first outer cylinder 3 and the outer periphery of the inner cylinder 1, whereby a first annular hermetic space 17 is formed between the inner side of the annular rearward end rib of the integrally secured first outer cylinder 3 and inner cylinder 1, the inner periphery of the first outer cylinder 3 and the outer periphery of the inner cylinder 1.

A second outer cylinder 3' having an annular forward end rib on the inner periphery at the forward end is provided on the outer periphery of the protruded part of the first slide cylinder 2, the protruded part of the first slide cylinder 2 is further protruded from the forward end of the second outer cylinder 3', and a second slide cylinder having an annular rearward end rib on the outer periphery at the rearward end is inserted into the second outer cylinder 3' to a deepest position and supported by the annular forward end rib of the second outer cylinder 3' where the annular reward end rib is reciprocally slidable in the axial direction along the inner periphery of the second outer cylinder 3'. An annular rearward end rib is provided on the inner periphery at the rearward end of the second outer cylinder 3'. The second outer cylinder 3' is integrally and firmly secured to the inner cylinder 1 through the annular reward end rib.

A second seal ring 12' is provided at the rearward side of the annular rearward end rib of the second slide cylinder 2' and in contact with the inner periphery of the second outer cylinder 3' and the outer periphery of the inner cylinder 1, whereby a second annular hermetic space 17' is formed between the inner side of the annular rearward end rib of the second outer cylinder 3', the inner periphery of the second outer cylinder 3' and the outer periphery of the inner cylinder 1. An elastic O ring 4 is expanded and mounted on the protruded forward end part of the first slide cylinder 2 from the forward end of the second outer cylinder 3'.

The endoscope-inserting cylinder 7 has a throughhole in the axial direction and is coaxially and firmly secured to the rearward end of the ligating device 20. The throughhole has the same diameter as that of the inner cylinder 1, through which an endoscope 6 is hermetically insertable from the rearward end of the endoscope-inserting cylinder 7 to the forward end of the inner cylinder 1. A first tube channel 18 is provided through the wall of the endoscope-inserting cylinder 7 and the rearward end of the ligating device 20 into the first annular hermetic space 17, whereby the first annular hermetic space 17 is communicated with a first outer tube 5, through which a fluid is introduced under pressure to the first annular hermetic space 17 from an outside source, thereby sliding the first slide cylinder 2 forwards, protruding the first slide cylinder 2 from the forward end of the inner cylinder 1 and forming a varix suction hole inside the protruded first slide cylinder 2. A second tube channel 5' is provided through the annular rearward end rib of the second outer cylinder 3' into the second annular hermetic space 17', whereby the second annular hermetic space 17' is communicated with a second outer tube 5', through which a fluid is introduced under pressure to the second annular hermetic space 17' from an outside source, thereby sliding the second slide cylinder 2' forwards and releasing the expanded elastic O ring 4 from the protruded forward end part of the first slide cylinder 2 by pushing the elastic O ring 4 with the second slide cylinder 2' and ligating a varix 16 sucked in the protruded first slide cylinder 2 with the released elastic O ring 4.

When the endoscope 6 is inserted into the common throughhole of the double slidable kit 20 having two slide cylinders 2 and 2' so that the forward end of the endoscope 6 can be slightly protruded from the forward end of the inner cylinder 1, as shown in FIG. 2A, or can be located to the same position as the forward end of the inner cylinder 1 or to a position slightly inner than the forward end of the inner cylinder 1, the narrowed sight of the endoscope encountered in the prior art can be overcome. The endoscope 6 provided with the present double slidable kit 21 at the forward end is inserted into the stomach or esophagus of a patient, and when the endoscope 6 catches sight of a varix to be ligated, the fluid is introduced under pressure into the first outer tube 5 to slide the first slide cylinder 2 forwards to protrude the first inner cylinder 2 from the forward end of the inner cylinder 1 as shown in FIG. 2B. The varix is sucked into the inner space within the protruded first slide cylinder 2 by suction. Then, another fluid is introduced under pressure into the second outer tube 5' to slide the second slide cylinder 2' forward and push the elastic O ring 4 with the second slide cylinder 2', thereby releasing the expanded elastic O ring 4 from the forward end of the protruded first slide cylinder 2 and ligating the sucked varix with the released elastic O ring 4.

The forward end region of the endoscope 6 is made flexible, where only the forward end part as long as about 20 mm inwardly from the forward end thereof is made not flexible. Thus, the slidable kit 21 must be provided at the forward end part so that the kit 21 may not prevent bending of the flexible forward end region of the endoscope 6. The length of the slidable kit 21 is also limited. In the case of the double sliding kit, two outer tubes, i.e. first and second outer tubes 5 and 5' for introducing fluids, respectively, are required, and thus the outer tubes preferably have shape and outer diameter so as not to be voluminous.

The length each of the inner cylinder 1, the first slide and second cylinders 2 and 2', and the first and second outer cylinders 3 and 3' of the double slidable kit 21 are so determined as to allow the second outer cylinder 3' and the elastic O ring 4 to be provided on the extended first slide cylinder 2' and allow the elastic O-ring 4 to be released from the forward end of the inner cylinder 1 by sliding the second slide cylinder 2' and pushing the elastic O ring 4 off the forward end of the inner cylinder 1 in view of the above-mentioned limited kit length.

In the double slidable kit 21, the annular rearward end rib can be provided each on the outer periphery of the inner cylinder 1 and the inner periphery of the first outer cylinder 3, the annular rearward end rib provided on the inner periphery of the first outer cylinder 3 can be longer forwards than the annular rearward end rib provided on the outer periphery of the inner cylinder 1, thereby defining the deepest position of the annular rearward end rib of the inserted first slide cylinder 2, or the annular rearward end rib can be provided on the outer periphery each of the first and second outer cylinders 3 and 3', the rearward side of which can be flat and the forward side of which can be in an L-shaped structure where the bottom end can be protruded forwards beyond the top end, thereby defining the deepest position of the annular rearward end rib of the inserted first and second slide cylinders 2 and 2', respectively, and a spring can be inserted each in the axial direction in spaces formed between the annular forward end ribs of the first and second outer cylinder 3 and 3' and the annular rearward ribs of the first and second slide cylinders 2 and 2', respectively. The first and second outer tubes 5 and 5' can be connected to syringes through connectors, respectively.

The present slidable kit for endoscopic ligation can give a broader endoscopic sight, and thus it is unnecessitated to insert only an endoscope into the stomach or esophagus of a patient to confirm the site of a varix to be ligate at first and then withdraw the endoscope, set a ligating kit to the endoscope and reinsert the endoscope provided with the ligating kit. Even if the forward end of the endoscope is turned, the expanded elastic O ring can be released to ligate the varix without fail, and washing of the alimentary canal with a washing solution and aspiration of the washing solution can be effectively carried out through the forceps channel of the endoscope at the same time. Thus, the present invention provides a useful instrument for safe, easy and assured endoscopic ligation by an operator.

What is claimed is:

1. A slidable kit for endoscopic ligation of gastric and esophageal varices, which comprises:

a) an outer cylinder having a rib on the inner periphery at the forward end;

b) a slide cylinder having a rib on the outer periphery at the rearward end, inserted into the outer cylinder;

c) an inner cylinder inserted into the slide cylinder, a rib being provided on at least one of the inner periphery at the rearward end of the outer cylinder and the outer periphery at the rearward end of the inner cylinder, through which the outer cylinder and the inner cylinder are integrated, d) a cylinder for fixing to an endoscope, the forward end of the cylinder being firmly secured to the rearward end of the integrated outer cylinder and the inner cylinder;

e) an elastic O ring expanded and mounted on the outer periphery at the forward end of the inner cylinder;

f) a seal ring provided at the rearward end of the inner cylinder, whereby an annular hermetic space is formed between the rearward ends of the outer cylinder, the inner cylinder and the slide cylinder;

g) a throughhole provided through the rearward end of the annular hermetic space; and h) a tube connected to the throughhole and serving as a fluid passage, a fluid being introduced under pressure into the annular hermetic space through the tube, thereby sliding the slide cylinder forwards, releasing the expanded O ring from the forward end of the inner cylinder by pushing with the slide cylinder and ligating a varix sucked in the inner cylinder with the released O ring.

2. A slidable kit according to claim 1, wherein the inner cylinder and the slide cylinder are extended in the axial direction; a second outer cylinder having ribs at the forward end and the rearward end is firmly secured on the outer periphery of the extended part of the slide cylinder while the forward end part of the extended slide cylinder is protruded from the forward end of the second outer cylinder; the elastic O ring is expanded and mounted on the outer periphery of the protruded forward end part of the slide cylinder; a second slide cylinder having a rib at the rearward end is inserted between the second outer cylinder and the extended inner cylinder; a second seal ring is provided at the rearward end of the second slide cylinder, whereby a second annular hermetic space is formed between the rearward ends of the second outer cylinder, the extended slide cylinder and the second slide cylinder; a second throughhole is provided at the rearward end of the second annular hermetic space; and a second tube connected to the second throughhole and serving a second fluid passage; the fluid is also introduced into the second annular hermetic space through the second tube from the outside source, thereby sliding the second slide cylinder forwards, releasing the expanded elastic R ring from the protruded forward end part of the slide cylinder and ligating a varix sucked in the inner cylinder with the released elastic O ring.

3. A single slidable kit for endoscopic ligation of gastric and esophageal varices, which comprises an endoscope-inserting cylinder and a ligating device coaxially and integrally secured to the endoscope-inserting cylinder;

the legating device comprising:

(a) an outer cylinder having an annular forward end rib on the inner periphery at the forward end;

(b) a slide cylinder having an annular rearward end rib on the outer periphery at the rearward end being inserted into the outer cylinder to a deepest position and supported by the annular forward end rib of the outer cylinder, the annular rearward end rib being reciprocally slidable in the axial direction along the inner periphery of the outer cylinder;

(c) an inner cylinder inserted into the outer cylinder through the slide cylinder therebetween, the forward end of the inner cylinder being protruded from the annular forward end of the outer cylinder, an annular rearward end rib being provided on at least one of the inner periphery at the rearward end of the outer cylinder and the outer periphery at the rearward end of the inner cylinder, the outer cylinder and the inner cylinder being integrally and firmly secured to each other through the annular rearward end rib;

(d) a seal ring provided at the rearward side of the annular rearward end rib of the slide cylinder and in contact with the inner periphery of the outer cylinder and the outer periphery of the inner cylinder, whereby an annular hermetic space is formed between the inner side of the annular rearward end rib of the integrally secured outer cylinder and inner cylinder, the inner periphery of the outer cylinder and the outer periphery of the inner cylinder; and (e) an elastic O ring expanded and mounted on the protruded forward end part of the inner cylinder from the forward end of the outer cylinder;

the endoscope-inserting cylinder having a throughhole for hermetically inserting an endoscope up to the forward end, coaxially and firmly secured to the rearward end of the ligating device, the throughhole being penetrated in the axial direction from the rearward end to the forward end;

a tube channel being provided through the wall of the endoscope-inserting cylinder and the rearward end of the ligating device into the annular hermetic space, whereby the annular hermetic space is communicated with an outer tube, through which a fluid is introduced under pressure to the annular hermetic space from an outside source, thereby sliding the slide cylinder forwards and releasing the expanded elastic O ring from the protruded forward end part of the inner cylinder by pushing the O-ring with the slide cylinder and ligating a varix sucked in the inner cylinder with the released elastic O ring.

4. A single slidable kit according to claim 3, wherein the annular rearward end rib is provided each on the outer periphery of the inner cylinder and the inner periphery of the outer cylinder, the annular rearward end rib provided on the inner periphery of the outer cylinder is longer forwards than the annular rearward end rib provided on the outer periphery of the inner cylinder, thereby defining the deepest position of the annular rearward end rib of the inserted slide cylinder.

5. A single slidable kit according to claim 3, wherein the annular rearward end rib is provided on the outer periphery of the outer cylinder, the rearward side of which is flat and the forward side of which is in an L-shaped structure where the bottom end is protruded forwards beyond the top end, thereby defining the deepest position of the annular rearward end rib of the inserted slide cylinder.

6. A single slidable kit according to claim 3, wherein a spring is inserted in the axial direction in a space formed between the annular forward end rib of the outer cylinder and the annular rearward end rib of the slide cylinder.

7. A single slidable kit according to claim 3, wherein the rearward end of the outer tube is connected to a syringe through a connector.

8. A double slidable kit for endoscopic ligation of gastric and esophageal varices, which comprises an endoscope-inserting cylinder and a ligating device coaxially and integrally secured to the endoscope-inserting cylinder;

the legating device comprising:

(a) a first outer cylinder having an annular forward end rib on the inner periphery at the forward end;

(b) a first slide cylinder having an annular rearward end rib on the outer periphery at the rearward end, inserted into the first outer cylinder to a deepest position and supported by the annular forward end rib of the first outer cylinder, the annular rearward end rib being reciprocally slidable in the axial direction along the inner periphery of the first outer cylinder, the forward end of the first slide cylinder being protruded from the forward end of the first outer cylinder;

(c) An inner cylinder inserted into the first outer cylinder through the first slide cylinder there-between, the forward end of the inner cylinder being protruded from the annular forward end of the first outer cylinder to the substantially same position as the forward end of the first slide cylinder at the deepest position, an annular rearward end rib being provided on at least one of the inner periphery at the rearward end of the first outer cylinder and the outer periphery at the rearward end of the inner cylinder, the first outer cylinder and the inner cylinder being integrally and firmly secured to each other through the annular rearward end rib;

(d) a first seal ring provided at the rearward side of the annular rearward end rib of the first slide cylinder and in contact with the inner periphery of the first outer cylinder and the outer periphery of the inner cylinder, whereby a first annular hermetic space is formed between the inner side of the annular rearward end rib of the integrally secured first outer cylinder and inner cylinder, the inner periphery of the first outer cylinder and the outer periphery of the inner cylinder;

(e) a second outer cylinder having an annular forward end rib on the inner periphery at the forward end being provided on the outer periphery of the protruded part of the first slide cylinder, the protruded part of the first slide cylinder being further protruded from the forward end of the second outer cylinder;

(f) a second slide cylinder having an annular rearward end rib on the outer periphery at the rearward end, inserted into the second outer cylinder to a deepest position and supported by the annular forward end rib of the second outer cylinder, the annular rearward end rib being reciprocally slidable in the axial direction along the inner periphery of the second outer cylinder, an annular rearward end rib being provided on the inner periphery at the rearward end of the second outer cylinder, the second outer cylinder being integrally and firmly secured to the first slide cylinder through the annular rearward end rib;

(g) a second seal ring being provided at the rearward side of the annular rearward end rib of the second slide cylinder and in contact with the inner periphery of the second outer cylinder and the outer periphery of the first slide cylinder, whereby a second annular hermetic space is formed between the inner side of the annular rearward end rib of the second outer cylinder, the inner periphery of the second outer cylinder and the outer periphery of the first slide cylinder; and (h) an elastic O ring expanded and mounted on the protruded forward end part of the first slide cylinder from the forward end of the second outer cylinder;

the endoscope-inserting cylinder having a throughhole in the axial direction and being coaxially and firmly secured to the rearward end of the ligating device, the throughhole having the same diameter as that of the inner cylinder, through which an endoscope is hermetically insertable from the rearward end of the endoscope-inserting cylinder to the forward end of the inner cylinder;

a first tube channel being provided through the wall of the endoscope-inserting cylinder and the rearward end of the ligating device into the first annular hermetic space, whereby the first annular hermetic space is communicated with a first outer tube, through which a fluid is introduced under pressure to the first annular hermetic space from an outside source, thereby sliding the first slide cylinder forwards, protruding the first slide cylinder from the forward end of the inner cylinder and forming a varix suction hole inside the protruded first slide cylinder;

a second tube channel being provided through the annular rearward end rib of the second outer cylinder into the second annular hermetic space, whereby the second annular hermetic space is communicated with a second outer tube, through which a fluid is introduced under pressure to the second annular hermetic space from an outside source, thereby sliding the second slide cylinder forwards and releasing the expanded elastic O ring from the protruded forward end part of the first slide cylinder by pushing the elastic O ring with the second slide cylinder and ligating a varix sucked in the protruded first slide cylinder with the released elastic O ring.

9. A double slidable kit according to claim 8, wherein the annular rearward end rib is provided each on the outer periphery of the inner cylinder and the inner periphery of the first outer cylinder, the annular rearward end rib provided on the inner periphery of the first outer cylinder is longer forwards than the annular rearward end rib provided on the outer periphery of the inner cylinder, thereby defining the deepest position of the annular rearward end rib of the inserted first slide cylinder.

10. A double slidable kit according to claim 8, wherein the annular rearward end rib is provided on the outer periphery each of the first and second outer cylinders, the rearward side of which is flat and the forward side of which is in an L-shaped structure where the bottom end is protruded forwards beyond the top end, thereby defining the deepest position of the annular rearward end rib of the inserted first and seconds slide cylinders.

11. A double slidable kit according to claim 8, wherein a spring is inserted each in the axial direction in spaces formed between the annular forward end ribs of the first and second outer cylinder and the annular rearward end ribs of the first and second slide cylinder, respectively.

12. A double slidable kit according to claim 8, wherein the rearward ends of the first and second outer tubes are connected to syringes through connectors, respectively.

\* \* \* \* \*